United States Patent [19]

Wang

[11] Patent Number: 5,526,810
[45] Date of Patent: Jun. 18, 1996

[54] INTRAVENTRICULAR MAPPING CATHETER

[76] Inventor: Dai-Yuen Wang, 21-18 147th St., Whitestone, N.Y. 11357

[21] Appl. No.: 133,728

[22] Filed: Oct. 7, 1993

[51] Int. Cl.⁶ .................................................. A61B 5/0402
[52] U.S. Cl. .................................................. 128/642
[58] Field of Search .................... 128/642; 607/122, 607/126, 128

[56] References Cited

U.S. PATENT DOCUMENTS

| | | | |
|---|---|---|---|
| 4,112,952 | 9/1978 | Thomas et al. | 607/128 |
| 4,172,451 | 10/1979 | Kline | 128/642 |
| 4,289,138 | 9/1981 | Halvorsen | 128/642 |
| 4,699,147 | 10/1987 | Chilson et al. | 128/642 |
| 5,156,151 | 10/1992 | Imran | 128/642 |
| 5,282,845 | 2/1994 | Bush et al. | 607/128 |
| 5,293,869 | 3/1994 | Edwards et al. | 128/642 |

*Primary Examiner*—Lee S. Cohen
*Attorney, Agent, or Firm*—Anderson Kill Olick & Oshinsky

[57] ABSTRACT

A intraventricular multielectrode catheter for mapping an activation sequence of a ventricle of a person's heart includes a plurality of solid mapping catheter elements, which have first expandable distal end portions, with a plurality of leads arranged along each of the first portions, and second portions bonded together and forming an inner tubing; a plurality of conductive wires extending along a longitudinal extend of each mapping catheter element and connected with its leads, respectively; a central skeleton element extending through the inner tubing and having at its distal end a tip cap to which the ends of the first portions are attached; and an outer flexible tube which surrounds the mapping catheter elements and is displaceable therealong for exposing a predetermined length of the first portions.

4 Claims, 2 Drawing Sheets

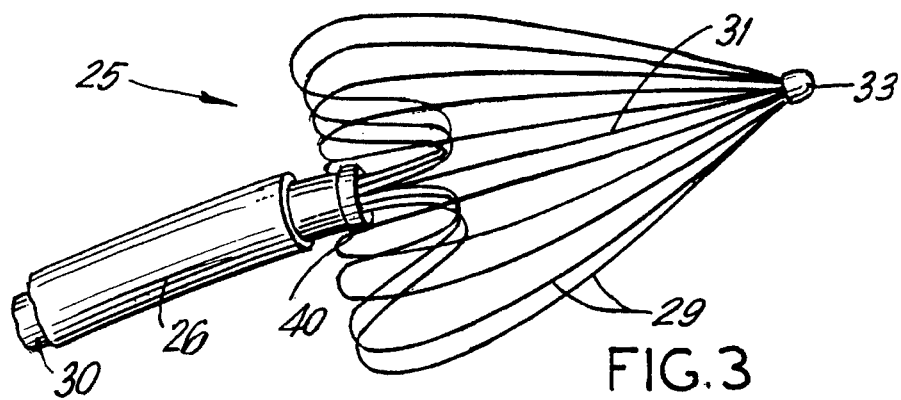
FIG. 3
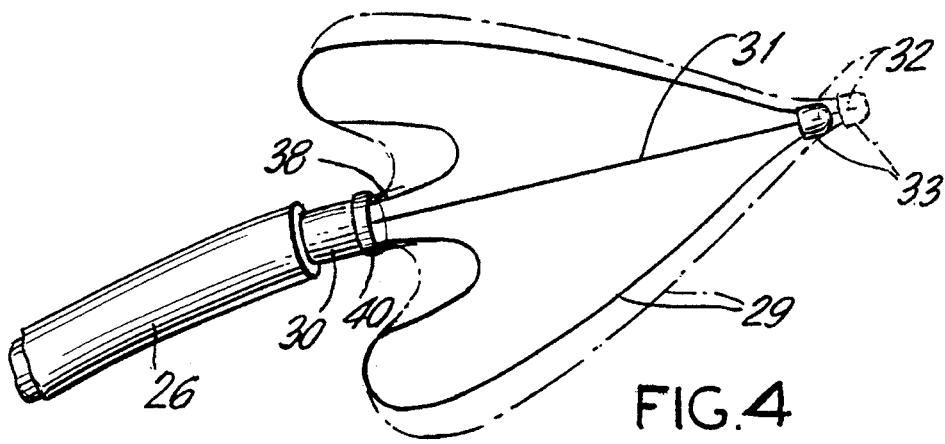
FIG. 4
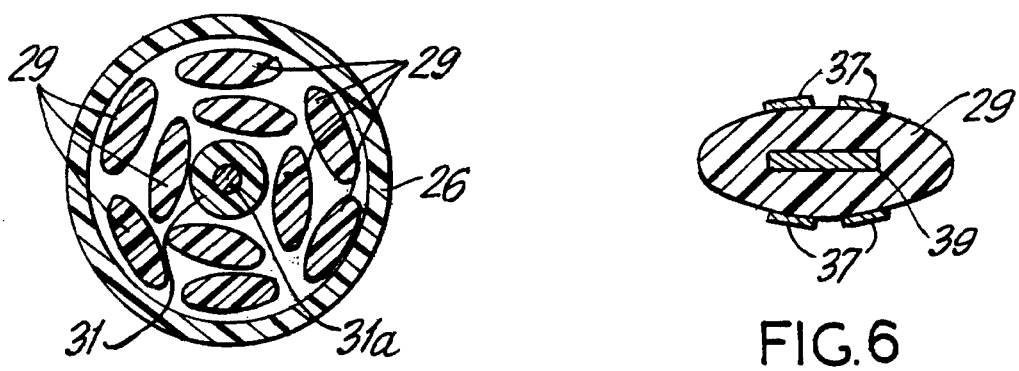
FIG. 5
FIG. 6
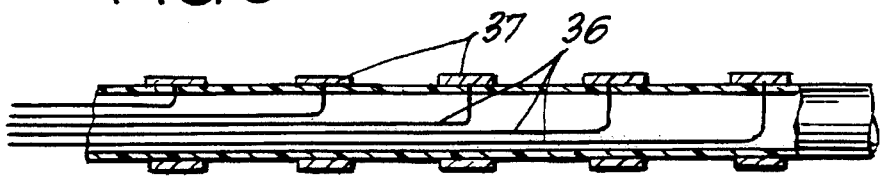
FIG. 7

INTRAVENTRICULAR MAPPING CATHETER

BACKGROUND OF THE INVENTION

1. Field of the Invention

The present invention relates to an intraventricular multielectrode catheter for mapping the activation sequence of a ventricle of a heart in order to locate ectopic foci (regions of abnormal electrical activity), which cause ventricular arrhythmia, and, in particular to a catheter which, in an expanded condition, has a shape approaching the shape of the ventricle.

2. Description of the Prior Art

Intraventricular mapping is a technique which permits spatial recording of electrical activity of a ventricle as a function of time in an endocardial manner, which can be done on a physiological condition (a condition of normal functioning of the heart). The information obtained by mapping is used for analysis of the activation sequence and the wave form, the potential distribution and, in particular, for localization of the ectopic foci during the depolarization and the repolarization.

A number of devices for the intraventricular mapping, which have multiple electrodes and can be inserted into the ventricle through the blood vessels, are known. Examples of such devices are disclosed in the following U.S. Pat. Nos. 3,326,207 (Egan), 3,825,015 (Berkovits), 3,903,897 (Woolons), 3,995,623 (Blake), 4,172,451 (Kline), 4,699,147 (Chilson), 5,215,103 (Desai).

Of these patents, only the Chilson patent discloses a catheter which, in an expanded condition, has a shape that can approaches the shape of the ventricle. Chilson discloses a catheter which consists of an outer flexible tubing, having an open proximal end and a distal end and four elongate wire assemblies which are received in the outer tubing and has six leads on the distal end of each wire assembly.

When the catheter is inserted into the ventricle, the wire assemblies expand to form an elliptical envelope. Upon expansion, the leads on the wire assemblies make contact with the endocardium to effect mapping. The Chilson device however, has a number of drawbacks. First, Chilson shows an elliptical envelope, formed by the wire assemblies in the expanded condition and which does not correspond to the cone shape of the ventricle. Since the envelope should form within only the ventricle (otherwise, it may compromise the cardiac function and damage the valve of the aorta by dilating the structure), only about half of the leads (that is 12 leads) can make contact with the endocardium. Considering the irregularity of the surface of the endocardium, the number of the leads making contact with the endocardium is even less than twelve, which is not enough for the mapping. Second, there is no mechanism in the Chilson catheter for absorbing the change in the ventricular volume during the contraction of the heart. Therefore, the contraction of the heart will cause the leads to change their position and even to lose their contact with the endocardium so that the measurement will be less reliable if at all possible. Third, Chilson's proposal to rotate the elliptical envelope to measure the electrical activity of the ventricle is practically impossible and potentially harmful because tendons and papillary muscles in the ventricles prevent such movement and the movement may also damage those structures. Also, the mapping is a spatial representation of the electrical activity as a function of time. When the electrical activity of the ventricle is measured in a different cardiac cycle by rotating the elliptical envelope, the time resolution of the measurement becomes less reliable.

Accordingly, a main object of the present invention is to provide a catheter which would overcome the above-discussed drawbacks.

Another object of the invention is to provide a catheter which, in an expanded condition, would have a shape substantially corresponding to the shape of the ventricle.

Yet another object of the invention is to provide a catheter which is able to absorb the change in the heart volume when the heart contracts.

Still another object of the invention is to provide a catheter having 100 or more leads to insure an accurate mapping.

A further object to the invention is to provide a catheter whose leads make contact with the entire surface of the endocardium.

Furthermore, an object of the invention is to provide a catheter whose leads make good contacts with the endocardium as during the contraction so during the relaxation of the heart, which requires that the catheter changes its shape to accommodate the change in the volume of the ventricle.

Additionally, an object of the invention is to provide a catheter which does not compromise the cardiac function when performing the intraventricular mapping under the physiological condition when being introduced into the ventricle.

SUMMARY OF THE INVENTION

These and other objects of the invention, which become apparent hereinafter, are achieved by providing a catheter which comprises a plurality of (preferably ten) relatively thin solid mapping catheter elements, wherein each element has twenty leads on the circumferential surface thereof and conductive wires printed on the surface of each catheter element, which extend along a longitudinal extent of the catheter element to respective leads. The wires are coated by a thin layer of insulating material. The catheter elements, upon expansion, assume a substantially heart-shaped envelope with its tip directed toward the apex and the folding part directed toward the atrium.

The folding part changes its shape to absorb the change in the volume of the ventricle during the cardiac contraction and therefore insures that the leads have a stable contact with the endocardium during the cardiac contraction and relaxation. The catheter, according to the present invention, provides more than one hundred leads for the intraventricular mapping and thus insures a better spatial and time resolution.

The catheter for the intraventricular mapping, according to the invention, comprises three main parts, namely, a central skeleton part, a flexible net-shaped mapping part and an outer tubing. The central part provides support for the net-shaped part.

The net-shaped part preferably is formed of ten mapping catheter elements having an expandable distal end portion length of approximately 10 cm, with twenty leads on each element. As a result, two hundred leads are available for the mapping. The net-shaped part is connected to the central part at its tip cap. The remaining portions of the respective mapping catheter elements form a tubing (defined as an inner tubing) connected by e.g., gluing. This tubing slides along the central skeleton part of the catheter. When the catheter is in the ventricle, with the tip touching the wall the outer tube is withdrawn a predetermined length and the inner tubing is then pushed along the central part, and the net-shaped portion of the catheter expands, occupying the respective ventricle volume to a heart-shape, with the tip toward the apex and the folding part toward the aorta and the atrium. The mapping catheter elements thus make contact with the ventricular wall. This allows the more than 100 leads (because of the irregularity of the surface of the endocardium, some leads may not make good contact with it) to make contact with the entire surface of the endocardium and therefore, provide for an accurate and adequate ventricular mapping.

When the heart contracts, the expandable part of the catheter will change its shape to absorb the change in the ventricular volume, maintaining a stable contact between the mapping catheter elements and the ventricle. The outer tubing controls the length of the mapping catheter portion by sliding along the catheter. The heart-shaped catheter portion should be opened only within the ventricle, below the juncture of tendon and the pilary muscle, so that the catheter does not interfere with the operation of the valves, does not damage the aorta, and can reach the area behind the mitral or tricuspid valve.

During insertion and withdrawal of the catheter, the outer tube can also be used to prevent the mapping catheter from being exposed to the wall and the valve of the aorta. Thereby, any possible damage to these structures is avoided. Adjusting the position of the tubing allows for a change in the exposed mapping catheter portion so that it fits the size of the ventricle. This arrangement makes a precise intraventricular mapping possible and the catheter, according to the present invention, provides on accurate information of the activation sequence of the ventricle and the location(s) of any abnormal electrical activity in the ventricular muscle. This is very important for the accurate diagnosis and further treatment of ventricular arrhythmia. The catheter of the invention can also be used to introduce a stimulus or some form of energy to the ventricle for diagnosis or ablation of ectopic foci.

BRIEF DESCRIPTION OF THE DRAWINGS

The features and objects of the present invention will become more apparent and the invention itself will be best understood from the following Detailed Description of the Preferred Embodiment, when read with reference to the accompanying drawings, wherein:

FIG. 3 is a perspective view of the catheter in a mapping position thereof;

FIG. 4 is a respective view showing a change in the shape of the mapping catheter elements in the mapping position thereof when the heart contracts (solid line) and relaxes (dash line);

FIG. 5 is a cross-sectional view of a mapping catheter portion at the juncture of the mapping catheter elements in the inner tubing;

FIG. 6 is a cross-sectional view of the mapping catheter element according to the invention at its distal end, with the mapping catheter element being covered by the outer tubing; and FIG. 7 is a partial elevational view, at an increased scale of an expandable portion of the mapping catheter element.

DETAILED DESCRIPTION OF THE PREFERRED EMBODIMENTS

Figure 1:
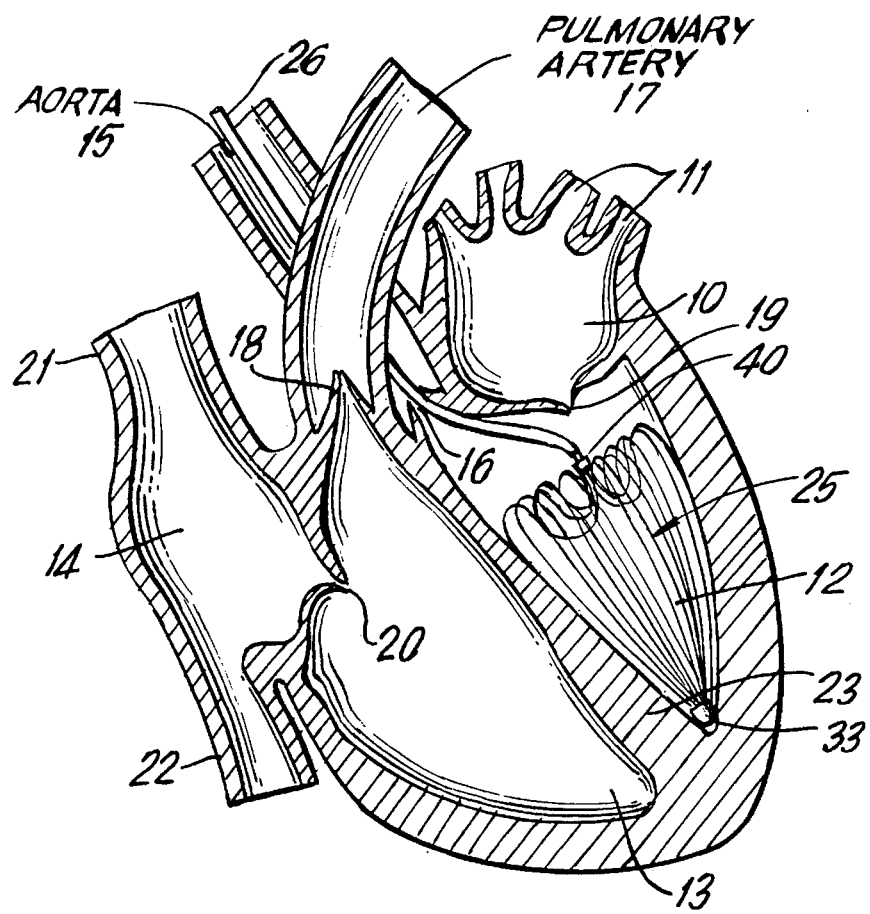
FIG. 1 is a cross-sectional view of a heart showing the mode of operation of the inventive catheter.

As shown in FIG. 1, a heart of a patient has a left atrium 10 with pulmonary veins 11, left ventricle 12, right ventricle 13 and right atrium 14. Aorta 15 connects with left ventricle 12 and contains the aorta valve 16. Pulmonary artery 17 connects with right ventricle 13 and contains the pulmonary artery valve 18. Left atrium 10 communicates with left ventricle 12 through mitral valve 19. Right atrium 14 communicates with right ventricle 13 through tricuspid vale 20. Superior vena cava 21 and inferior vena cava 22 lead into right atrium 14. Myocardial wall 23 separates the left and right ventricles. Catheter 25 and the technique of passing it through the heart chambers will be described in detail below.

Figure 2:
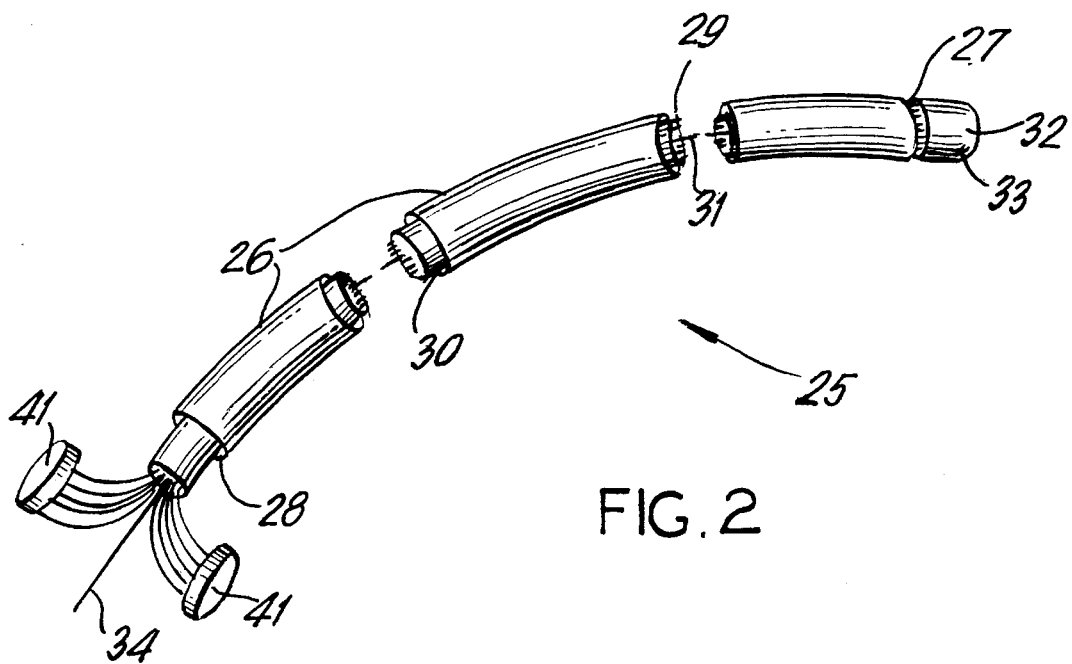
FIG. 2 is a perspective view of the catheter according to the present invention, with the mapping catheter elements covered by the outer tube and portions broken away.

As shown in FIG. 2, the catheter 25 includes an outer tubing 26, having an open distal end 27 and an open proximal end 28. A plurality of thin mapping catheter elements 29, except their distal end portions of a length of about 10 cm, are connected together, e.g., by gluing, to form an inner tubing 30, which is located in the outer tubing 26. A central skeleton part or piece 31 is arranged centrally of the inner tubing 30 and has a distal end 32, with a tip cap 33 and a proximal end 34, which extends out of the proximal end of the inner tubing 30. The distal ends of the mapping catheter elements 29 are secured in the tip cap 33 of the central skeleton piece 31. The outer tube 26 can slide along the inner tubing 30, exposing a different length of the mapping catheter elements 29. The outer tube 26 can be made of a suitable plastic material, e.g., polyurethane or polytetrafluoroethylene.

The mapping catheter elements 29 can be made of a solid, but flexible rods, with conductive wires 36 printed on the rod surface or with thin conductive wires placed into shallow grooves formed in the rod surface. The conductive wires then are coated with a thin insulating plastic material, which may be the same material as used for the manufacture of the outer tubing.

Each conductive wire is exposed at certain location of the mapping catheter element and is connected to a corresponding lead 37 at the respective location, which is printed over the wire. Each mapping catheter element may have up to twenty such locations and, thus, twenty leads. The leads 37 are printed on the circumference of a rod. This arrangement provides a strong catheter and allows the shape of the cross-section of the mapping position of the catheter to change as needed, even at different parts thereof. For example, the cross-section of the mapping catheter element can be elliptical, as shown in FIG. 6, though a round cross-section also can be used, which makes good use of the limited space within the inner tubing of the catheter so that more mapping catheter elements may be incorporated into the inner tubing.

Different materials can also be incorporated into certain part of the mapping catheter element to make it stronger. For example, a small piece of stainless steel wire 38 can be secured to the catheter element at the junctures between the mapping catheter elements, which form the inner tubing, and non-bonded expandable end portions to prevent forming of a sharp angle at the juncture when the inner tubing 30 slides down along the central skeleton piece 31 and changes its shape during the cardiac contraction. This is also important for smooth retraction of the mapping catheter elements. A similar reinforcing element (39) can be incorporated into the expandable portion of the mapping catheter element to give it enough strength to keep the mapping part in good contact with the endocardium during the ventricular contraction and relaxation. The metal wires incorporated into the mapping catheter elements should have a shape such that they permit the mapping catheter elements to expand outwardly and upwardly, assume a heart shape and reach the areas behind the mitral or tricuspid valve. Some material can also be incorporated into the mapping catheter elements in a different manner to make them identifiable and distinguishable from one another on X-ray.

A metal ring 40 is added at the juncture of the expandable portions of the mapping catheter elements and the inner tubing to prevent the tubing from slitting.

At the proximal end of the catheter, the mapping catheter elements which form the tubing become separate and are connected to a recording system by one or several connectors 41 which have totally two hundred pins in total connected to respective conductive wires 36 of leads 37 of the mapping catheter elements. The pins in the connector are arranged in such manner that each lead from a given mapping catheter element can be easily identified with the recording system.

The material for the making of the mapping catheter elements should be strong enough to maintain its shape and keep a stable contact with the endocardium. It should also be flexible and soft enough for the ventricle to contract normally. This property, as noted above, can be obtained by incorporating metal wire into the catheters elements. As the net-shaped portion becomes heart-shaped, spaces are created between the thinner catheters, guaranteeing that the catheter will not block the outlet of the ventricle. All the above properties allow for the intraventricular mapping without compromising the cardiac function.

The central skeleton piece is made of polyurethane, with the thin stainless steel wire 31a incorporated in its center and a tip cap 33 on its distal end. There is a lead on the cap which is connected to the stainless steel wire and can pick up electrical signal for the mapping. Fixed to the tip cap are the mapping catheter elements. The tip cap 33 will form the tip of the heart-shaped catheter. A proximal part of the central skeleton piece 31 is made stronger for the manipulation of the inner tubing. The proximal part stays out of the human body when the catheter is inserted into the ventricle.

During the intraventricular mapping, the catheter with the mapping catheter element covered by the outer tube is introduced into the chamber of the left ventricle through the artery or/and the chamber of the right ventricle through the vein. When the distal end of the catheter is in the chamber, with its tip cap 33 touching the wall of the tip of the ventricular chamber, the outer tubing is pulled back to a location beneath the juncture of the tendon with the papillary muscle to expose the non-bonded end portions of the mapping catheter elements 29 in such manner that the exposed portion of the mapping catheter is within the chamber. The inner tubing (30) is then pushed along the central skeleton piece (31) until the net-shaped mapping catheter elements assume a heart-shape, with the tip toward the apex and the expandable part toward the atrium. This allows more than one hundred leads on the mapping catheter elements to make contact with the entire surface of the endocardium and spatially record the electrical activity of the ventricle as a function of time, which can be used for identifying some electrophysiological variable such as activation sequence, conducting a waveform analysis, and determining potential distribution. A stimulus or train of stimuli can also be introduced to the ventricular muscle for a special diagnostic or study purpose. Some kind of energy, such as DC current or radio frequency, can also be introduced through the leads to a part of the ventricle containing the identified ectopic foci. After the procedure is finished, the inner tubing is pulled back until the mapping catheter elements 29 are in their retracted position, and the outer tube 26 is pushed down to cover the mapping catheter elements. The catheter is then withdrawn.

While a particular embodiment of the invention has been shown and described, various modifications thereof will be apparent to those skilled in the art and, therefore, it is not intended that the invention be limited to the disclosed embodiment or to the details thereof and departures may be made therefrom within the spirit and scope of the invention as described in the appended claims.

What is claimed is:

1. An interventricular multielectrode catheter for mapping an activation sequence of a ventricle of a person's heart, said catheter comprising:

a plurality of solid flexible mapping catheter elements having each a first expandable distal portion and a second portion, said second portions being bonded together forming an inner tubing;

a plurality of leads arranged along the first expandable distal portion of each mapping catheter element for engaging with an endocardium of the ventricle;

a plurality of conductive wires extending along a longitudinal extent of each mapping catheter element and connected with said plurality of leads, respectively;

a central skeleton member extending through said tubing and having, at a distal end thereof, a tip cap, to which distal ends of said first portions are attached, said inner tubing being displaceable along said skeleton member;

a flexible outer tube surrounding said mapping catheter elements and displaceable there along from said tip cap of said central skeleton member for exposing a predetermined length of said first portions, which corresponds to a size of the ventricle, said first portions expanding upon being exposed, by displacement of said inner tubing toward said tip cap, and assuming a shape substantially corresponding to a shape of the ventricle; and connector means for connecting said conductive wires to a recording apparatus.

2. A catheter as set forth in claim 1, wherein said plurality of solid mapping catheter elements comprises ten elements, and said plurality of leads comprises twenty leads arranged on a circumference of each mapping catheter element.

3. An interventricular multielectrode catheter for mapping an activation sequence of a ventricle of a person's heart, said catheter comprising:

a plurality of solid flexible mapping catheter elements having each a first expandable distal portion and a second portion, said second portions being bonded together forming an inner tubing;

a plurality of leads arranged along the first expandable distal portion of each mapping catheter element for engaging with an endocardium of the ventricle;

a plurality of conductive wires extending along a longitudinal extent of each mapping catheter element and connected with said plurality of leads, respectively;

a central skeleton member extending through said tubing and having, at a distal end thereof, a tip cap, to which distal ends of said first portions are attached, said inner tubing being displaceable along said skeleton member;

a flexible outer tube surrounding said mapping catheter elements and displaceable there along from said tip cap of said central skeleton member for exposing a predetermined length of said first portions, which corresponds to a size of the ventricle, said first portions expanding upon being exposed and assuming a shape substantially corresponding to a shape of the ventricle;

connector means for connecting said conductive wires to a recording apparatus; and wherein each of said mapping catheter elements has an oval cross-section and includes a reinforcing element extending along an axis thereof.

4. An interventricular multielectrode catheter for mapping an activation sequence of a ventricle of a person's heart, said catheter comprising:

a plurality of solid flexible mapping catheter elements having each a first expandable distal portion and a second portion, said second portions being bonded together forming an inner tubing;

a plurality of leads arranged along the first expandable distal portion of each mapping catheter element for engaging with an endocardium of the ventricle;

a plurality of conductive wires extending along a longitudinal extent of each mapping catheter element and connected with said plurality of leads, respectively;

a central skeleton member extending through said tubing and having, at a distal end thereof, a tip cap, to which distal ends of said first portions are attached, said inner tubing being displaceable along said skeleton member;

a flexible outer tube surrounding said mapping catheter elements and displaceable there along from said tip cap of said central skeleton member for exposing a predetermined length of said first portions, which corresponds to a size of the ventricle, said first portions expanding upon being exposed and assuming a shape substantially corresponding to a shape of the ventricle;

connector means for connecting said conductive wires to a recording apparatus;

a ring surrounding said inner tubing at an end thereof adjacent to a juncture of said tubing with said first portions; and wherein each of said mapping catheter elements has a reinforcing ship of a short predetermined length attached thereto and extending therealong from said ring.

* * * * *

UNITED STATES PATENT AND TRADEMARK OFFICE
CERTIFICATE OF CORRECTION

PATENT NO. : 5,526,810
DATED : June 18, 1996
INVENTOR(S) : Dai-Yuan Wang

It is certified that error appears in the above-indentified patent and that said Letters Patent is hereby corrected as shown below:

Title page, item 76], "Inventor: Dai-Yuen Wang, 21-18 147th St. Whitestone, N.Y. 11357." should read -- Inventor: Dai-Yuan Wang, 138-49 Elder Avenue, Apt. 11-H, Flushing, New York 11355.--

Signed and Sealed this

Second Day of June, 1998

Attest:

BRUCE LEHMAN

Attesting Officer

Commissioner of Patents and Trademarks